United States Patent
Yamada et al.

(10) Patent No.: US 7,442,844 B2
(45) Date of Patent: Oct. 28, 2008

(54) PROCESS FOR PRODUCING ISOPRENE

(75) Inventors: Osamu Yamada, Tokyo (JP); Manabu Kusano, Kamisu (JP); Nobuo Takayanagi, Kamisu (JP); Hideki Arimoto, Tainai (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 542 days.

(21) Appl. No.: 10/551,596

(22) PCT Filed: Mar. 24, 2004

(86) PCT No.: PCT/JP2004/004038

§ 371 (c)(1),
(2), (4) Date: Nov. 1, 2005

(87) PCT Pub. No.: WO2004/087625

PCT Pub. Date: Oct. 14, 2004

(65) Prior Publication Data

US 2007/0106104 A1 May 10, 2007

(30) Foreign Application Priority Data

Mar. 31, 2003 (JP) .............................. 2003-095152

(51) Int. Cl.
*C07C 1/00* (2006.01)
*C07C 1/207* (2006.01)

(52) U.S. Cl. ............... 585/609; 585/603; 585/606; 585/607; 585/608; 585/639; 585/642

(58) Field of Classification Search ................. 585/603, 585/606, 607–609, 639, 642
See application file for complete search history.

(56) References Cited

U.S. PATENT DOCUMENTS

| 3,972,955 | A | 8/1976 | Halcour et al. |
| 4,511,751 | A | 4/1985 | Ninagawa et al. |
| 4,593,145 | A | 6/1986 | Ninagawa et al. |

FOREIGN PATENT DOCUMENTS

| JP | 50-62905 | | 5/1975 |
| JP | 59-70623 | A | 4/1984 |
| RU | 2 128 637 | C1 | 4/1999 |

*Primary Examiner*—Glenn Caldarola
*Assistant Examiner*—In Suk Bullock
(74) *Attorney, Agent, or Firm*—Leydig, Voit & Mayer, Ltd.

(57) ABSTRACT

A process for producing isoprene is provided, which includes continuously or intermittently supplying isobutylene and/or t-butanol, formaldehyde and water into an acidic aqueous solution, and reacting the reaction mixture while distilling away a mixture containing produced isoprene, water, unreacted starting materials and other low boiling point components from this reaction mixture to the outside of the reaction system, wherein the reaction is carried out while controlling the concentration of high boiling point byproducts, which is produced and accumulated in the reaction mixture, to fall within the range of 0.5-40 mass %.

10 Claims, 2 Drawing Sheets

PROCESS FOR PRODUCING ISOPRENE

TECHNICAL FIELD

The present invention relates to a process for producing isoprene. Isoprene obtained by the production method of the present invention is used effectively as a basic chemical starting material for various chemical products and materials of polymers.

BACKGROUND ART

As the production method of isoprene, a method comprising continuously or intermittently supplying isobutylene and/or t-butanol (hereinafter "isobutylene and/or t-butanol" is sometimes to be abbreviated as "$C_4$"), formaldehyde and water to a reactor containing an acidic aqueous solution, and carrying out a reaction while distilling away the produced isoprene together with water and other low boiling point components to the outside of the reaction system is known (e.g., JP-A-59-70623).

In addition, a production method is known, wherein, in the production method described in JP-A-59-70623, a part of a mixture of $C_4$, formaldehyde, water and acidic aqueous solution (hereinafter to be abbreviated as a "reaction mixture") is taken out from the reactor, heated together with at least a part of $C_4$, and then introduce the mixture into the reactor again (e.g., JP-A-59-190930). Note that "water" may be understood to be contained as an aqueous solution such as an acidic aqueous solution and the like, and the "reaction mixture" may contain a reaction product and by-products.

In addition, a production method of isoprene is known, which is characterized in that, in the production method described in JP-A-59-70623, the quantity of heat of water is recovered by fractionally condensing mostly water in the produced isoprene, water, unreacted starting materials and other low boiling point components, which are distilled away from the reaction system as a gas (hereinafter the "produced isoprene, water, unreacted starting materials and other low boiling point components" is to be abbreviated as a "reaction distillation gas"), the quantity of heat of an uncondensed gas is used as a heat source for vaporizing isobutylene, a heat source for recovering unreacted isobutylene by distillation from the organic layer obtained by concentration and phase separation of the reaction distillation gas, and the like (e.g., JP-A-60-4138).

Furthermore, a process for producing isoprene is known, which is characterized in that, for separation of high boiling point byproducts accumulated in a reaction mixture, a residue or a part thereof, which is obtained by evaporating unreacted starting materials and isoprene from an organic layer of a distillate during the reaction, is added to the reaction mixture or a part thereof, and the organic layer containing the high boiling point byproducts are separated from an acidic aqueous solution (e.g., JP-A-59-116236).

However, the present inventors have studied the above-mentioned conventional production methods of isoprene and newly found the following problems in these production methods.

To be specific, by simply performing the production methods described in JP-A-59-70623, JP-A-59-190930 and JP-A-59-116236, the concentration of high boiling point byproducts in the reaction mixture shows variation, which in turn unstabilizes the concentration of acid in the reaction mixture, and causes corrosion of apparatuses and degraded results of reaction to produce isoprene.

Particularly, it was found that, when a part of a reaction mixture is drawn from a reactor and heated together with at least a part of $C_4$, the heat is not sufficiently transmitted to the reaction mixture at a concentration too high or too low of high boiling point byproducts in the reaction mixture. When the heat is not sufficiently transmitted, the temperature of the reaction mixture in the reactor becomes gradually low, and the amount of water distilled during the reaction tends to decrease. For continuous reaction, therefore, the amount of the aqueous formaldehyde solution to be supplied needs to be reduced to constantly maintain the surface of the reaction mixture at a certain level, which in turn often decreases the amount of producing isoprene per unit time.

On the other hand, when the temperature of the reaction mixture in the reactor is constantly maintained at a certain level in this situation by excessively heating the reaction mixture drawn from the reactor and at least a part of $C_4$, some drawbacks occur including lower use efficiency of the quantity of heat necessary for the production of isoprene, easy clogging of pipe lines with high boiling point byproducts accumulated therein and the like.

In the process described in JP-A-60-4138, the quantity of heat possessed by a reaction distillation gas can be effectively recovered and reused. However, it is not satisfactory as a supplement to the quantity of heat necessary for producing isoprene, and there is a room for improvement prior to industrial practice.

It is therefore an object of the present invention to solve the above-mentioned problems and provide a process capable of producing isoprene more efficiently than conventional processes.

DISCLOSURE OF THE INVENTION

The present invention achieves the above-mentioned object by the following characteristics.

(1) A process for producing isoprene, which comprises continuously or intermittently supplying isobutylene and/or t-butanol, formaldehyde and water into an acidic aqueous solution, and reacting the reaction mixture while distilling way a mixture comprising produced isoprene, water, unreacted starting materials and other low boiling point components from this reaction mixture to the outside of the reaction system, wherein the aforementioned reaction is carried out while controlling the concentration of high boiling point byproducts, which is produced and accumulated in the aforementioned reaction mixture, to fall within the range of 0.5-40 mass %.

(2) The process for producing isoprene of the above-mentioned (1), wherein the concentration of the high boiling point byproducts in the reaction mixture is controlled to fall within the above-mentioned range by forming a outlet for taking out the reaction mixture in a reactor containing the reaction mixture, taking out a part of the reaction mixture from the outlet, and separating and removing at least a part of the high boiling point byproducts from the reaction mixture, since then introducing the left reaction mixture again into the reactor.

(3) The process for producing isoprene of the above-mentioned (2), wherein the outlet for taking out the reaction mixture is formed at least in the bottom of the reactor.

(4) The process for producing isoprene of the above-mentioned (2) or (3), wherein the outlet for taking out the reaction mixture is formed in the side wall of the reactor, and the level of the outlet is set such that the volume of the reaction mixture filled to the level is not less than ½ of the total volume of the reaction mixture during the production of isoprene.

(5) The process for producing isoprene of the above-mentioned (1)-(4), wherein the mixture containing produced isoprene, water, unreacted starting materials and other low boiling point components is distilled away from the reaction system as a reaction distillation gas, water is fractionally condensed from the reaction distillation gas, and the obtained water is introduced into the reactor again to control the concentration of the high boiling point byproducts in the reaction mixture to fall within the above-mentioned range.

(6) The process for producing isoprene of the above-mentioned (1)-(5), wherein the concentration of the high boiling point byproducts in the reaction mixture is controlled to fall within the above-mentioned range by installing, on the reactor, a stirring apparatus having a stirring blade designed to horizontally rotate in the reaction mixture, and supplying isobutylene and/or t-butanol toward the stirring blade from an inlet formed by extending a pipe line to directly below the stirring blade in the reactor.

(7) The process for producing isoprene of the above-mentioned (1)-(6), wherein the concentration of the high boiling point byproducts in the reaction mixture is controlled to fall within the above-mentioned range by installing, on the reactor, a stirring apparatus having a stirring blade designed to horizontally rotate in the reaction mixture, in which a part of the reaction mixture is taken out from the reactor, heated with at least a part of isobutylene and/or t-butanol in a heat exchanger and introduced again into the reactor, and supplying the heated reaction mixture toward the stirring blade from an inlet formed in the reactor.

BRIEF DESCRIPTION OF THE DRAWINGS

The meanings of the symbols indicated in FIG. 1 and FIG. 2 are described in the following. A: reaction mixture, P1-P10: pipe lines, 1: reactor, 2, 3, 5, 6, 7, 11 and 12: heat exchangers, 4: high boiling point byproducts separation tank, 8, 9 and 13: distillation receiving tank, 10, 14: distillation tower.

BEST MODE FOR EMBODYING THE INVENTION

Figure 1:
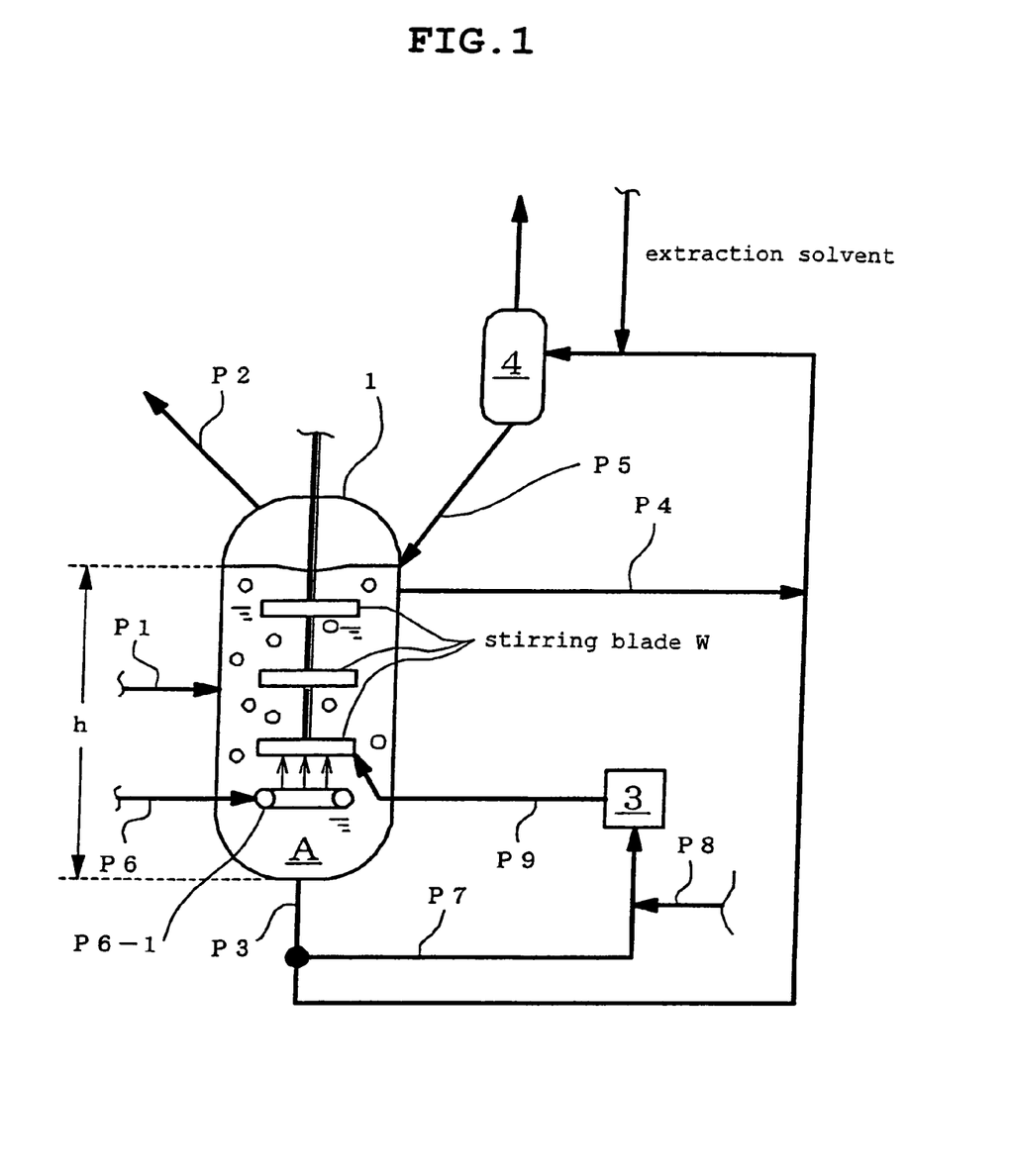
FIG. 1 is a schematic view of a production equipment to explain the production method of the present invention.

In the process for producing isoprene of the present invention, as schematically shown in the schematic view of the production equipment of FIG. 1, $C_4$ is continuously or intermittently supplied from a pipe line P6, and formaldehyde and water from a pipe line P1 to an acidic aqueous solution in a reactor 1, and a reaction mixture A is reacted while distilling away, from this reaction mixture A, a mixture containing produced isoprene, water, unreacted starting materials and other low boiling point components to the outside of the reaction system from a distillation pipe line P2 as a reaction distillation gas. The basic technique for this production method is the same as that in conventionally known isoprene production technique, and reference may be made to the aforementioned JP-A-59-70623, JP-A-59-190930, JP-A-60-4138 and JP-A-59-116236.

Here, the unconventional important characteristics of the present invention rest in the fact that the aforementioned production of isoprene is performed while controlling the concentration of the high boiling point byproducts in the aforementioned reaction mixture A (not illustrated), which is produced and accumulated in said reaction mixture, to fall within the range of 0.5-40 mass %.

For example, JP-A-59-70623 describes removal of a high boiling point byproducts, which is accumulated during reaction, and operation thereof, but does not at all describe the influence of the concentration of high boiling point byproducts on the results of the reaction. In contrast, in the present invention, a new action and effect has been found, which can be afforded by allowing the presence of a given amount of high boiling point byproducts in the reaction mixture, and the invention is characterized by the control of the removal operation of the high boiling point byproducts such that its concentration falls within the range of 0.5-40 mass %.

The high boiling point byproducts, of which concentration is to be controlled, is generally widely dispersed in the liquid in a reactor. Depending on the stirring efficiency, however, it may be unequally distributed in the upper part or lower part of the reaction mixture. While the components of the high boiling point byproducts cannot be specified, organic compounds having high boiling point (e.g., polymers of the product and byproducts in the process for producing isoprene of the present invention and the like), raw materials, impurities such as inorganic substance derived from the reaction apparatus and the like, and the like can be mentioned.

By controlling the concentration of the high boiling point byproducts in the reaction mixture to fall within the range of 0.5-40 mass %, the high boiling point byproducts preferably act as heat transmission mediums. Thus, the efficiency of heating of the reaction mixture using a heat exchanger and the like can be maintained at a preferable level, and, moreover, troubles such as clogging of pipe line due to high boiling point byproducts and the like do not occur. As a result, isoprene can be produced more efficiently than before.

The concentration of the high boiling point byproducts in the reaction mixture is more preferably within the range of 1-30 mass %, and particularly preferably within the range of 2-20 mass % for simultaneously achieving improved heat changeability and suppression of troubles such as clogging of pipe line and the like.

When the concentration of the high boiling point byproducts in the reaction mixture is less than 0.5 mass %, the heating efficiency of the reaction mixture decreases, which in turn decreases the temperature of the reaction mixture in the reactor, decreases the distillation amount of water, and decreases the amount of the aqueous formaldehyde solution to be supplied into the reactor to maintain the level of the reaction mixture in the reactor at a certain level, whereby the amount of producing isoprene per unit time decreases. To prevent the aforementioned temperature of the reaction mixture in the reactor from decreasing, the reaction mixture may be excessively heated in a heat exchanger. However, this method causes problems, including degraded efficiency of use of the quantity of heat necessary for isoprene production, clogging of pipe lines with high boiling point byproducts, due to the accumulation of the high boiling point byproducts in the pipe lines, and susceptibility to corrosion by acid due to the temperature near the surface of the heat exchanger, which becomes too high.

On the other hand, concentration of high boiling point byproducts, which exceeds 40 mass %, causes problems, including easily clogging of pipe lines connecting the heat exchanger and the reactor, internal pipe lines of the heat exchanger itself and the like, thus causing a trouble in operation, lower efficiency of heating (efficiency of giving heat) of the reaction mixture in a heat exchanger, and easy concentration of a circulating reaction mixture, to corrode apparatus due to the highly concentrated acid, and the like.

While the method for controlling the concentration of the high boiling point byproducts in the reaction mixture to fall within the above-mentioned range is not particularly limited, for example, a kind of feed-back control comprising taking out a part of the reaction mixture (hereinafter the reaction mixture thus taken out is sometimes to be referred to as a "taken-out reaction mixture"), removing at least a part of the high boiling point byproducts from the taken-out reaction mixture by an appropriate removal treatment method mentioned below, and returning the taken-out reaction mixture after the removal treatment (hereinafter sometimes to be referred to as a "reaction mixture after removal treatment") into the reactor is a convenient control method. In the example of FIG. 1, a reaction mixture is taken out from pipe lines P3 and/or P4, high boiling point byproducts are separated and removed in high boiling point byproducts separation tank 4, and the reaction mixture after removal treatment is returned from the pipe line P5 into the reactor.

While the method of separating and removing the high boiling point byproducts from the reaction mixture in the high boiling point byproducts separation tank 4 is not particularly limited, for example, an extraction method using an organic solvent can be preferably used.

The taking out a part of the reaction mixture in the reactor may be continuously or intermittently performed. In addition, the amount of taken-out reaction mixture can be determined in consideration of the accumulated amount of high boiling point byproducts in a reactor and the like. As a method of taking out the reaction mixture, for example, a method comprising controlling the concentration of high boiling point byproducts in a reaction mixture to fall within the range of 0.5-40 mass % while continuously taking out the reaction mixture at 2 L/hr in a reactor having an inner volume of 120 L and the like can be mentioned.

The method of measuring the concentration of high boiling point byproducts in the reaction mixture is not particularly limited. Since high boiling point byproducts solidify when a part of the reaction mixture is taken out and cooled, for example, a method comprising separating the solidified high boiling point byproducts, measuring its mass and calculating the concentration of the high boiling point byproducts in the reaction mixture, and the like can be mentioned.

Formaldehyde to be used in the present invention is supplied as an aqueous solution to a reactor. From the aspect of reducing the quantity of heat to be given to the accompanying water, or the quantity of heat necessary for the production of isoprene, the concentration of the aqueous formaldehyde solution is preferably as high as possible. The concentration of the aqueous formaldehyde solution is generally preferably within the range of 20-70 mass %, more preferably within the range of 25-60 mass %. When the concentration of the aqueous formaldehyde solution is too high, the problem that paraformaldehyde is easily precipitated occurs.

$C_4$ to be used in the present invention may include 3-methylbutane-1,3-diol, 3-methyl-2-buten-1-ol, 3-methyl-3-buten-1-ol, 3-methyl-1-buten-3-ol, methylisopropylketone, 2-methylbutanal, methyl-t-butylformal, 4,4-dimethyl-1,3-dioxane, 4-methyl-5,6-dihydro-2H-pyran and the like. In addition, it may include methyl-t-butyl ether and the like, which are decomposed to isobutylene and t-butanol under reaction conditions.

The acidic aqueous solution to be used in the present invention is an aqueous solution of acidic substances such as inorganic acid, organic acid, a salt thereof, and the like. As the acidic substance, those low volatile or non-volatile under reaction conditions are preferable. For example, inorganic acids (phosphoric acid, sulfuric acid, boric acid and the like), heteropolyacids (silicotungstic acid, phosphotungstic acid and the like), organic acids (p-toluenesulfonic acid, benzenesulfonic acid, trifluoromethanesulfonic acid, oxalic acid and the like), acidic salts (sodium hydrogensulfate and the like) and the like can be mentioned.

While the pH of the acidic aqueous solution may vary depending on the kind of the acidic substance, reaction temperature, the rate of supplying $C_4$, the rate of supplying formaldehyde and the like, it is generally preferably within the range of pH 0.5-2.5, more preferably within the range of pH 1-2.

In the process for producing isoprene of the present invention, the reaction can be carried out while simultaneously supplying, besides a reaction mixture, low boiling point compounds inactive under reaction conditions or inert gas into a reactor as necessary. As such low boiling point compounds, hydrocarbons are preferable, particularly those having 1 to 10 carbon atoms, such as n-propane, n-butane, n-hexane, cyclohexane and the like. As the inert gas, nitrogen and the like are preferable.

The molar ratio of $C_4$ and formaldehyde to be supplied to a reactor (hereinafter to be referred to as "$C_4$/formaldehyde") is preferably not less than 3, more preferably not less than 5. While the molar ratio does not have an upper limit in a strict sense, an excessively large molar ratio provides only a small improvement effect of the yield of isoprene. Conversely, it is economically disadvantageous because the quantity of heat used for the production of isoprene increases. Generally, $C_4$/formaldehyde is preferably not more than 20, more preferably not more than 12. When $C_4$/formaldehyde is less than 3, the yield of isoprene tends to decrease.

As is clear from the above-mentioned molar ratio of $C_4$ and formaldehyde, $C_4$ is used in a surplus as against formaldehyde in the present invention. In the production method of the present invention, therefore, the excess amount of $C_4$ supplied to the reactor is distilled away in an unreacted state as a reaction distillation gas together with the produced isoprene, low boiling point components and water to the outside of the reaction system. The unreacted $C_4$ distilled away to the outside of the reaction system can be separated/recovered from other distillation components and reused for the production method of the present invention.

The unreacted $C_4$ distilled away to the outside of the reaction system has a composition similar to the equilibrium composition of isobutylene and t-butanol under reaction conditions. Even when only one of isobutylene and t-butanol is supplied to a reactor as a starting material in the production method of the present invention, if an unreacted starting material is separated/recovered and reused for reducing the basic unit of the starting material, it is comparable to the use of a mixture of isobutylene and t-butanol as a starting material.

As mentioned above, in the present invention, a method is employed, comprising continuously or intermittently supplying $C_4$, formaldehyde and water into an acidic aqueous solution, and carrying out a reaction while distilling away a mixture containing produced isoprene, water, unreacted starting materials and other low boiling point components from this reaction mixture as reaction distillation gas to the outside of the reaction system.

To obtain isoprene in a high yield, it is preferable that the pressure in the reactor (when low boiling point compounds inactive under the reaction conditions are supplied together with the starting materials, the pressure after subtracting the partial pressure) is within the range of 1.1 to 2.5 times, more preferably 1.1 to 2 times, the vapor pressure of an acidic aqueous solution at the reaction temperature.

The vapor pressure of an acidic aqueous solution at the reaction temperature (hereinafter to be abbreviated as Pw) is a physical constant unambiguously determined based on the kind and concentration of an acidic substance contained in the reaction mixture. When the pressure in the reactor exceeds 2.5 times the Pw, the yield of isoprene tends to show a remarkable decrease. On the other hand, when the pressure in the reactor is less than 1.1 times the Pw, the yield of isoprene does not show a remarkable decrease, but the conversion ratio of formaldehyde decreases and the ratio of water to isoprene in the reaction distillation gas increases. This causes an increase in the quantity of heat consumed in the reaction, namely, the quantity of heat necessary for the production of isoprene, which is economically disadvantageous.

The preferable reaction temperature in the present invention is determined in consideration of the concentration of acid in the reaction mixture, and is generally preferably within the range of 150-220° C. When the reaction temperature is less than 150° C., the yield of isoprene tends to decrease even when the concentration of an acidic aqueous solution is increased to maintain the reaction rate at a constant level. On the other hand, even when the reaction temperature exceeds 220° C., the selectivity of isoprene does not decrease markedly; however, the conversion ratio of formaldehyde under the conditions affording an optimal selectivity decreases. Conversely, when such reaction conditions as may increase the conversion ratio of formaldehyde are selected, successive reactions from isoprene proceed to increase byproducts, which in turn disadvantageously decreases the selectivity of isoprene.

The preferable supply rate of formaldehyde source (aqueous formaldehyde solution) to a reactor is determined in consideration of the concentration of acid in the reaction mixture, reaction temperature and reaction pressure.

To increase the supply rate of formaldehyde source, the concentration of acid in the reaction mixture needs to be increased, or the reaction temperature needs to be elevated. In this case, the problem of corrosion of the reactor occurs. While the supply rate of formaldehyde source has no lower limit, too small the supply rate causes degradation of volume efficiency. Thus, the supply rate of formaldehyde source is generally preferably within the range of 0.2-3 mol/hr, more preferably within the range of 0.5-2 mol/hr, converted into formaldehyde, per 1 kg of the reaction mixture.

The amount of water to be supplied to a reactor is generally controlled such that the amount of the reaction mixture in a reactor is maintained at a constant level. Therefore, this amount is determined by the amount of water distilled from a reactor and the amount of water increased or decreased by the reaction.

As mentioned above, since, of the components constituting the reaction distillation gas, water has a high boiling point, when the pressure in the reactor is high, the ratio of water to the total of the components other than water in the reaction distillation gas decreases, and when the pressure is low, the ratio of water increases. Therefore, it can be said that the ratio of mols of water distilled from the reactor and mols of distilled starting materials and products is defined by the pressure in the reactor. In addition, since the mols of distilled starting materials and products are almost identical to the mols of $C_4$ to be supplied, the ratio of distilled water to $C_4$ to be supplied can be also defined by the pressure in the reactor. Therefore, the amount of water to be supplied can be determined in consideration of the pressure in the reactor, the amount of $C_4$ to be supplied and increase or decrease of water due to the reaction.

As mentioned above, high boiling point byproducts are formed and accumulated in a reaction mixture while the reaction is carried out for a long time. Since high boiling point byproducts show phase separation and are dispersed in a reaction mixture, a part of the reaction mixture in a reactor is continuously or intermittently taken out and led to high boiling point byproducts separation tank (e.g., decanter, extraction tower and the like) to remove at least a part of the high boiling point byproducts, whereby its concentration is controlled.

However, since the specific gravity of this high boiling point byproducts are only slightly different from that of the reaction mixture and a byproduct having high specific gravity as compared with the reaction mixture and a byproduct having a small specific gravity as compared with the reaction mixture are present in the mixture therein, separation by a separating operation utilizing difference in the specific gravity, such as decantation and the like, is difficult. Since high boiling point byproducts solidify at room temperature, a method comprising once lowering the temperature of a reaction mixture to allow solidification of the high boiling point byproducts and then removing the byproduct by separation may be employed. In this case, an quantity of heat needs to be given again to the reaction mixture. From these aspects, extraction removal using an extraction solvent is preferable to facilitate separation of high boiling point byproducts from a reaction mixture.

As such extraction solvents, hydrocarbon having a lower boiling point than that of water, having lower solubility in water, and liquid at normal pressure is preferable, such as n-hexane, cyclohexane and the like.

As the extraction solvents, a compound obtained as a distillation residue after distillation of unreacted starting materials and isoprene from an organic substance contained in the reaction distillation gas distilled from a reactor to the outside of the reaction system, or a subset of components therein can be used. As the compound contained in the distillation residue, 4-methyl-5,6-dihydro-2H-pyran, methylisopropylketone, 2-methylbutanal, 2,6-dimethyl-2,5-heptadiene, 2,6-dimethyl-1,5-heptadiene, 3-methyl-3-buten-2-ol and the like can be mentioned. Besides these, a compound having 4 to 15 carbon atoms and various functional groups can be mentioned.

When the production method of the present invention is performed, a heating apparatus may be set on a reactor itself to secure the quantity of heat necessary for the production of isoprene and the quantity of heat necessary for the distillation of isoprene, water, unreacted starting materials and other low boiling point components. An embodiment installing a suitable auxiliary heating apparatus is preferable. As shown in FIG. 1, for example, an embodiment to heat the reaction mixture by a constitution in which a heat exchanger 3 is installed as an auxiliary heating apparatus on the outside of the reactor, and a reaction mixture circulates between the reactor 1 and the heat exchanger 3 through pipe lines P7 and P9, and the like can be mentioned.

In this embodiment, when a reaction mixture is heated by direct circulation thereof in an outside heat exchanger, the boiling point of the reaction mixture in the heat exchanger is high as compared to the reaction mixture in the reactor because the amount of isobutylene dissolved in the reaction mixture in the heat exchanger is small, which in turn results in a strikingly elevated temperature of the reaction mixture in the heat exchanger. Such temperature elevation of the reaction mixture increases side reactions, which then reduces the yield of isoprene. To prevent this, as shown in FIG. 1, an embodiment wherein at least a part of $C_4$ is added through pipe line P8 to the reaction mixture taken out from pipe line P7 for circulation, they are heated together in a heat exchanger 3 and introduced into the reactor 1 through pipe line P9 is preferable.

However, t-butanol has a markedly small effect of preventing the temperature elevation of a reaction mixture due to heating as compared to isobutylene. In addition, since t-butanol is converted to isobutylene upon contact with an acidic aqueous solution in the heat exchanger, and then first shows the aforementioned effect, as $C_4$ to be added to the reaction mixture taken out for heating by circulation, isobutylene is preferable.

In the present invention, an quantity of heat possessed by a reaction distillation gas can be recovered and effectively utilized for the production of isoprene.

Figure 2:
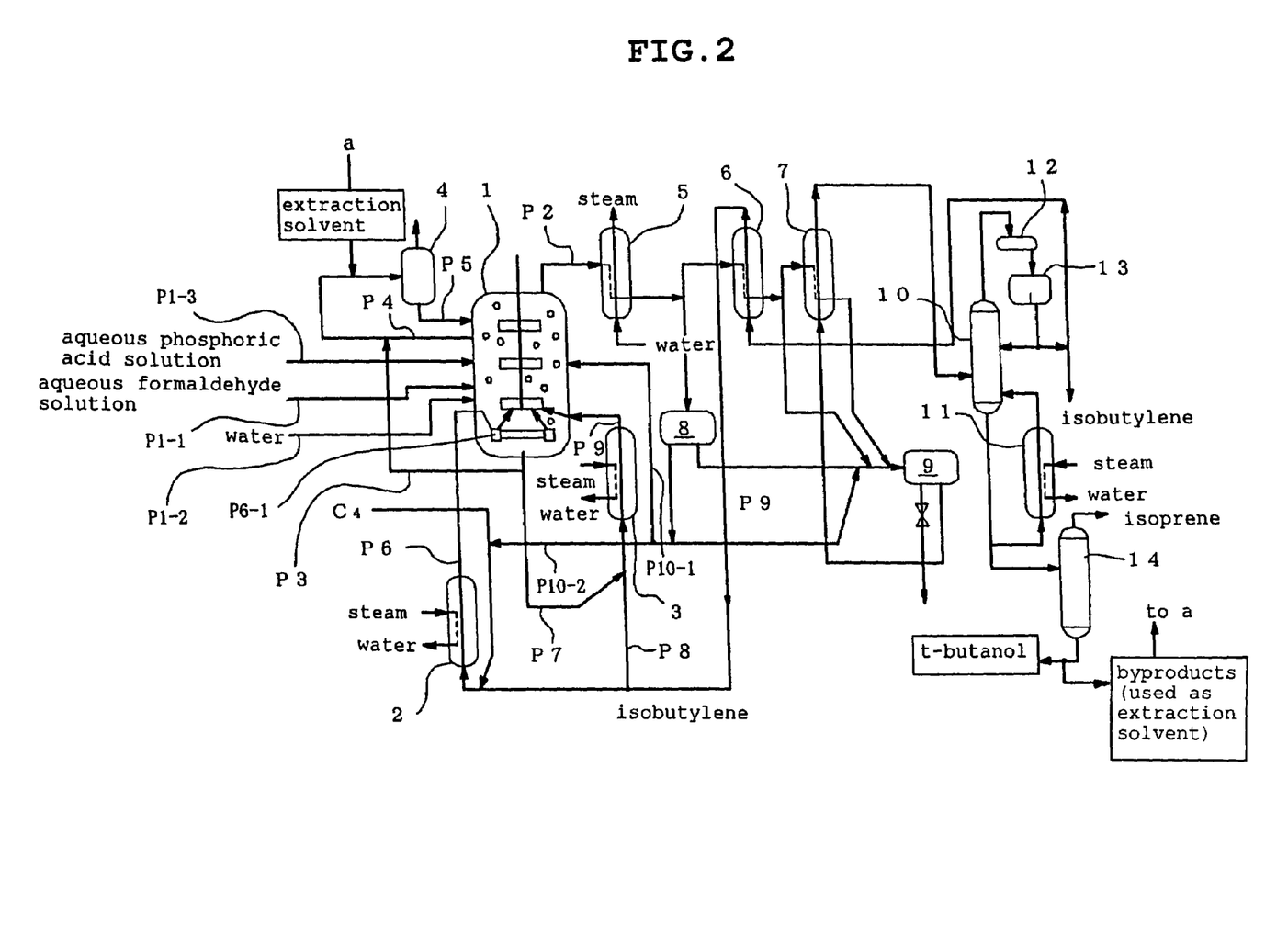
FIG. 2 is a schematic view showing the constitution of the equipment constructed to practice the production method of the present invention in Examples of the present invention. In the heat exchangers 2, 3, 5, 6, 7 and 11 shown therein, connections in the heat exchanger are schematically shown with solid lines and broken lines to clarify the input/output relationship of the pipings, but they do not show the shape of the inside piping.

As an embodiment of recovery of the quantity of heat, for example, an embodiment where the quantity of heat possessed by water is recovered by fractionally condensing mostly water in a reaction distillation gas can be mentioned (e.g., in FIG. 2, water is fractionally condensed in a heat exchanger 5).

As the use of the recovered quantity of heat, use of an quantity of heat of an uncondensed reaction distillation gas as a heat source to vaporize isobutylene (e.g., a heat source in heat exchangers 6 and 7 in FIG. 2), use as a heat source to recover unreacted isobutylene in an organic layer obtained by condensation and phase separation of a reaction distillation gas by distillation (e.g., a heat source in heat exchanger 11 in FIG. 2) and the like, use as a heat source to generate steam by heat exchange of a reaction distillation gas with water, use of a reaction distillation gas as a heat source of a reboiler of a distillation tower used for recovery of isobutylene, recovery of t-butanol or recovery or purification of isoprene, by directly introducing the gas into the reboiler and the like can be mentioned. In FIG. 2, the steam obtained by a heat exchanger 5 can be used as a steam for heating in a heat exchanger 11 and the like.

To control the concentration of the high boiling point byproducts in a reaction mixture to fall within the range of 0.5-40 mass %, the present invention comprises a step of continuously or intermittently introducing a part of the reaction mixture into a decanter, extraction tower and the like and removing at least a part of the high boiling point byproducts from the reaction mixture, as mentioned above.

Since the removal method of the high boiling point byproducts is important in the present invention, the present inventors have further studied the invention. As a result, they have found that some of the accumulated byproducts having a high boiling point have high specific gravity as compared with the reaction mixture and others have a low specific gravity as compared with the reaction mixture as mentioned above, and in a reactor, high boiling point byproducts which have high specific gravity as compared with the reaction mixture tend to reside in the lower part of the reaction mixture, namely, on the bottom of the reactor, and high boiling point byproducts which have a low specific gravity tend to reside in the upper part of the reaction mixture.

In a preferable embodiment of the present invention, therefore, an outlet for taking out the reaction mixture is formed at least in the bottom of the reactor for removal of the high boiling point byproducts in the reaction mixture. In FIG. 1, for example, a pipe line P3 for taking out a reaction mixture is formed in the center of the bottom of the reactor. Using this pipe line P3, a high boiling point byproducts which have high specific gravity as compared with the reaction mixture can be easily removed from the reactor when a part of the reaction mixture is continuously or intermittently taken out. While the outlet is preferably formed in the center of the bottom of the reactor, it is not limited to this position, and one or more outlets may be formed at position(s) sufficiently low to take out high boiling point byproducts which have high specific gravity as compared with the reaction mixture.

Similarly, in a preferable embodiment of the present invention, to facilitate taking out of high boiling point byproducts which have low specific gravity as compared with the reaction mixture, an outlet for taking out the reaction mixture is formed on the sidewall of the reactor (sidewall of the body of reactor). In this case, the level of the outlet is preferably set such that the volume of the reaction mixture filled to the level is not less than ½, more preferably not less than ⅔, of the total volume of the reaction mixture to be contained at the time of start of the production (hereinafter to be abbreviated as height h). Forming an outlet for taking out the reaction mixture at this height h, high boiling point byproducts which have low specific gravity as compared with the reaction mixture can be easily removed when a part of the reaction mixture is continuously or intermittently extracted.

Forming outlets for taking out the reaction mixture on both the bottom and the sidewall of the reactor, high boiling point byproducts can be efficiently removed from the reaction mixture in a reactor, regardless of the specific gravity, and the concentration of high boiling point byproducts can be more easily controlled to fall within the range of 0.5-40 mass %.

When even a single outlet for taking out the reaction mixture is not formed in the bottom of the reactor, high boiling point byproducts which have high specific gravity as compared with the reaction mixture is accumulated on the bottom of the reactor during the course of reaction for a long time, and control of the concentration of the high boiling point byproducts in the reaction mixture to fall within the range of 0.5-40 mass % becomes difficult. Then, problems of degraded efficiency of heating the reaction mixture and blockade of pipe lines, as well as inability to maintain steady state of reaction due to variations in the acid concentration and composition ratio of starting materials in a reaction mixture and the like occur.

In addition, when an outlet for taking out the reaction mixture is not formed on the sidewall of the reactor, a high boiling point byproducts which have low specific gravity as compared with the reaction mixture is accumulated in the upper part of the reaction mixture during the course of reaction for a long time, and control of the concentration of the high boiling point byproducts to fall within the range of 0.5-40 mass % becomes difficult. Then, distillation of produced isoprene, water, unreacted starting materials and other low boiling point components as a reaction distillation gas from the reaction mixture to the outside of the reactor is prevented, and a problem of inability to maintain steady state of reaction due to an increased level of the reaction mixture in a reactor and variations in the acid concentration and composition ratio of starting materials in a reaction mixture and the like occurs. Furthermore, when the amount of the reaction distillation gas decreases, the amount of the aqueous formaldehyde solution to be supplied to the reactor needs to be reduced to maintain the level of the reaction mixture in a reactor, which in turn reduces the production amount of isoprene.

One embodiment of a preferable constitution of the reaction apparatus to control the concentration of the high boiling point byproducts in the reaction mixture to fall within the range of 0.5-40 mass % is explained by using FIG. 1. A stirring apparatus (outside driving device is not shown) is installed such that a stirring blade W horizontally rotates in a reaction mixture in a reactor, a pipe line P6 to supply $C_4$ is extended to right beneath the stirring blade in a reactor, and $C_4$ is supplied preferably by being squirted toward the stirring blade from the inlet P6-1.

The distance between the stirring blade and a inlet for supplying $C_4$ is not limited in a strict sense as long as $C_4$ hits the stirring blade; from the aspect of efficiency of dispersing $C_4$, for example, when a distance from the rotation center of a stirring blade to the tip is 2 m, the distance is generally preferably within the range of not more than 0.3 m, more preferably within the range of not more than 0.2 m. When $C_4$ is supplied without hitting the stirring blade, dispersion of gas and liquid in a reaction mixture in a reactor becomes insufficient, the amount of produced high boiling point byproducts increases and the concentration of high boiling point byproducts accumulated in the reaction mixture tends to increase.

While the form of the inlet P6-1 for supplying $C_4$ is not particularly limited, in a preferable embodiment, a tube constituting the inlet P6-1 is bent like a ring, and some holes for supplying $C_4$ are formed on its circumference at suitable intervals. In this case, the ring-shaped inlet P6-1 preferably has a curve radius of 50-80% of the distance between the rotation center of the stirring blade to the tip thereof. In addition, the interval of the holes formed on the circumference of the ring-shaped inlet P6-1 is preferably a distance corresponding to about $1/5$-$1/100$ of the length of the circumference, more preferably about $1/10$-$1/40$ of the length of the circumference.

As mentioned above, it is preferable to add $C_4$ to the reaction mixture, heat the mixture using an outside heat exchanger, and return the mixture again to the reactor, during circulation of a reaction mixture between the reactor and the outside heat exchanger (pipe lines P7, P8, P9 in FIG. 1).

In a preferable mode of returning the reaction mixture to the reactor, for example, the reaction mixture after addition of $C_4$ and heating in a heat exchanger 3 is introduced into the lower part of the reactor via pipe line P9 and supplied such that it hits a stirring blade W, as shown in FIG. 1. In this way, gas and liquid in a reaction mixture in a reactor are sufficiently dispersed, an increase in the concentration of high boiling point byproducts can be suppressed and the concentration of high boiling point byproducts can be easily controlled. Here, the lower part of the reactor is not particularly limited as long as the reaction mixture hits the stirring blade when introducing the reaction mixture again into the reactor. Preferably, it is introduced into the reactor from the lower side of the stirring blade.

When the reaction mixture returned to a reactor from the heat exchanger via pipe line P9 is not supplied in such a manner as hits the stirring blade, gas and liquid in a reaction mixture in a reactor are not sufficiently dispersed, and the amount of produced high boiling point byproducts increase and the byproducts are accumulated in the reactor, which leads to the propensity toward increased concentration of high boiling point byproducts thereof in the reaction mixture.

In the present invention, the water obtained by fractional condensation from the reaction distillation gas may be reused as the water to be supplied to the reactor (hereinafter the water to be fractionally condensed from the reaction distillation gas and reused is to be abbreviated as "recycle water"). For example, in FIG. 2, the water fractionally condensed in the heat exchanger 5 is introduced into a distillation receiving tank 8, supplied to a reactor via pipe line P10-1 and the like and reused.

By directly supplying the recycle water to the reactor, the amount of the reaction mixture in a reactor can be maintained at a constant level, and the concentration of high boiling point byproducts in the reaction mixture can be easily controlled to fall within the range of 0.5-40 mass %. Since the temperature of the recycle water is within the range of 120-140° C. (under the condition of a pressure of about 1.5 MPa), the quantity of heat necessary for the production of isoprene can be reduced. When the recycle water is not used, or when fresh water (generally about 25° C.) is used, while the concentration of the high boiling point byproducts in the reaction mixture can be controlled, it is economically disadvantageous since the quantity of heat necessary for heating to the reaction temperature increases.

Isoprene can be obtained by fractionating the organic layer of the substance distilled away to the outside of the reaction system by the present reaction method. The steps of ultimate fractionation of isoprene from the distillate distilled away from pipe line P2 in FIG. 1 are known by reference to well-known techniques (e.g., JP-A-60-4138 and the like).

The present invention is explained in detail in the following by referring to Examples, which are not to be construed as limitative.

In the following Examples, equipments necessary for practicing the process for producing isoprene of the present invention were actually constructed, the concentration of high boiling point byproducts in a reaction mixture was controlled to be stable at various concentrations within the range of 0.5-40 mass %, the reaction was continued for 8 hrs while maintaining the concentration at each level, and examined for the conversion of formaldehyde, and selectivity and yield of isoprene, for the last 1 hr at each concentration.

In Comparative Examples, the concentration of high boiling point byproducts in the reaction mixture in a reactor was set to a level outside the above-mentioned ranges, and the critical significance of the concentration range of the high boiling point byproducts was confirmed by comparison with example.

[Equipment Constitution]

First, one embodiment of the equipments constructed to practice the process for producing isoprene of the present invention is explained in FIG. 2.

A tank (inner volume 120 L) was prepared as a reactor 1, to which a pipe line P6 for introducing $C_4$, a pipe line P1-1 for introducing an aqueous formaldehyde solution, a pipe line P1-2 for introducing water, a pipe line P1-3 for introducing an acidic aqueous solution (aqueous phosphoric acid solution), a distillation pipe line P2 for products etc. and pipe lines P3 and P4 for taking out a reaction mixture were connected. The reactor was equipped with accessory devices necessary for the control of the reaction, such as a thermometer, a pressure gauge, a stirrer, a baffle and the like.

To the reactor 1 were supplied 46 mass % aqueous formaldehyde solution, 2.5% aqueous phosphoric acid solution as an aqueous acidic solution and 12-fold mols of water relative to formaldehyde. On the other hand, 8-fold mols of $C_4$ relative to formaldehyde was preheated in a heat exchanger 2 to allow evaporating, and supplied by squirting $C_4$ toward the stirring blades in the reactor from the ring inlet for supplying $C_4$.

In addition, a constitution was employed, in which a pipe line P7 was branched from a pipe line P3 for taking out the reaction mixture, the reaction mixture taken out from the reactor was mixed with $C_4$, the resulting mixture was heated in a heat exchanger 3, and returned to the reactor. The reaction mixture heated in the heat exchanger 3 was squirted toward the stirring blades to hit the blades, when it was returned to the reactor 1.

Isoprene produced in the reactor 1 is distilled to the outside of the reactor as a reaction distillation gas through a pipe line P2 together with unreacted $C_4$, water, formaldehyde and the like. The reaction distillation gas is delivered to a heat exchanger 5. In the heat exchanger 5, heat exchange occurs between the reaction distillation gas flown into a piping for heat exchange and cooling water flown into the heat exchanger (or the reaction distillation gas is cooled), whereby water in the reaction distillation gas is fractionally condensed. In addition, the cooling water allowed to flow into the heat exchanger 5 becomes steam with the quantity of heat obtained from the reaction distillation gas, whereby the quantity of heat is collected.

Water fractionally condensed in the heat exchanger 5 is delivered to a distillation receiving tank 8.

A part of the water in the distillation receiving tank 8 is directly supplied to the reactor though a pipe line P10-1, used for controlling the amount of reaction mixture in a reactor, also supplied to a heat exchanger 2 through a pipe line P10-2, used for controlling the molar ratio of formaldehyde and $C_4$, evaporated together with $C_4$ and supplied to the reactor 1. The remaining water in the distillation receiving tank 8 is delivered to a distillation receiving tank 9.

On the other hand, a compound that was not condensed in the heat exchanger 5 is condensed in heat exchangers 6 and 7, delivered to a distillation receiving tank 9, where it is separated into an organic layer and an aqueous layer. The organic layer is delivered to the heat exchanger 7, heated and delivered to a distillation tower 10 for separation of isobutylene.

The fraction in the distillation tower 10 mainly contains isobutylene, which is condensed in a heat exchanger 12 and delivered to a distillation receiving tank 13.

A part of the fraction containing isobutylene as a main component is heated in the heat exchanger 6 to allow evaporating, a part thereof is delivered to a heat exchanger 2 to control the molar ratio with formaldehyde, and another part is delivered to a heat exchanger 3 to prevent increase in the boiling point in the heat exchanger 3 and then returned to the reactor 1. The rest of the fraction is returned to the distillation tower 10, or separately reused as a starting material for the production method of the present invention by the way of a purification step of isobutylene.

The bottom solution of the distillation tower 10 contains isoprene and unreacted t-butanol as main components. Isoprene is obtained from the tower top by purification of this bottom solution of the distillation tower 10 in a distillation tower 14.

The main component of the bottom solution in the distillation tower 14 is t-butanol, which is separately purified and reused for the production method of the present invention. The byproduct obtained on this occasion is delivered to high boiling point byproducts separation tank 4 and used as an extraction solvent for the separation of high boiling point byproducts from the reaction mixture taken out from the reactor.

The reaction mixture (including high boiling point byproducts) in the reactor 1 is taken out from each outlet for taking out formed at the center of the bottom of the reactor and on the sidewalls of the reactor near the level of the reaction mixture and, after mixing with the aforementioned extraction solvent, delivered to high boiling point byproducts separation tank 4, where it is separated into the organic layer (extraction solvent) comprising high boiling point byproducts and an aqueous layer.

The organic layer is effectively used for fuels and the like, and at least a part of the aqueous phosphoric acid solution in the aqueous layer is recycled to the reactor.

The reaction mixture can be sampled for the measurement of the concentration of high boiling point byproducts in the reaction mixture in a reactor by, for example, forming outlets for taking out in the pipe lines P3, P4 and P7. In the employed constitution, the reaction mixture can be taken out or not taken out from the outlets, thereby to control the concentration of high boiling point byproducts in the reaction mixture to fall within the range of 0.5-40 mass % while confirming the concentration thereof.

EXAMPLES 1-8

The reaction conditions in the reactor were reaction temperature 175-178° C., reaction pressure 1.52 MPa and rotation of stirring blade 48-55 rpm revolutions/min.

To a reactor (inner volume 120 L) was supplied 2.5% aqueous phosphoric acid solution (60 L), and thereto were continuously supplied 46 mass % aqueous formaldehyde solution at 3.24 kg/hr, isobutylene at 17.7 kg/hr, t-butanol at 6.02 kg/hr and water at 9.08 kg/hr under the above-mentioned reaction conditions to start the reaction.

After 24 hrs from the start of the reaction, the concentration of a high boiling point byproducts in the reaction mixture was controlled to the below-mentioned predetermined values by controlling the amount of removal of high boiling point byproducts mainly in high boiling point byproducts separation tank 4, in a reaction equipment shown in FIG. 2, wherein one outlet for taking out the reaction mixture is formed at the center of the bottom of the reactor and one outlet is formed on the side (at a level corresponding to 4/5 of the whole volume of the reaction mixture in the reactor), $C_4$ is squirted from the inlet P6-1 for introducing to hit the stirring blades, when the reaction mixture is returned to the reactor via pipe line P9, it is squirted to hit the stirring blades, and recycle water is introduced again into the reactor from the distillation receiving tank 8.

The controlled concentrations of the controlled byproducts having a high boiling point are as follows. 0.5 mass % (Example 1), 1 mass % (Example 2), 2 mass % (Example 3), 5 mass % (Example 4), 10 mass % (Example 5), 20 mass % (Example 6), 30 mass % (Example 7), 40 mass % (Example 8).

The reaction was maintained in a stable state at each concentration and then continued for 8 hrs. The conversion ratio of formaldehyde, and the selectivity and yield of isoprene were examined for the last 1 hr. The results are shown in Table 1.

Comparative Examples 1-4

In the same manner as in Examples 1-8, the reaction was carried out except that the concentrations of byproducts having a high boiling point in the reaction mixture were set to 0 mass % (Comparative Example 1), 0.3 mass % (Comparative Example 2), 50 mass % (Comparative Example 3) and 60 mass % (Comparative Example 4), the conversion ratio of formaldehyde and the selectivity and yield of isoprene were examined for the last 1 hr. The results are shown in Table 1.

TABLE 1

|  |  | Concentration of high boiling point byproducts (mass %) | Conversion ratio of formaldehyde (%) | Selectivity of isoprene (%) | Yield (%) |
|---|---|---|---|---|---|
| Example | 1 | 0.5 | 98.1 | 72.4 | 71.0 |
|  | 2 | 1 | 98.2 | 72.4 | 71.2 |
|  | 3 | 2 | 98.3 | 72.5 | 71.4 |
|  | 4 | 5 | 98.3 | 72.7 | 71.5 |
|  | 5 | 10 | 98.3 | 72.8 | 71.9 |
|  | 6 | 20 | 98.5 | 73.0 | 71.6 |
|  | 7 | 30 | 98.6 | 72.5 | 71.3 |
|  | 8 | 40 | 98.8 | 72.3 | 71.0 |
| Comp. | 1 | 0.1 | 95.8 | 72.2 | 69.2 |
| Example | 2 | 0.3 | 96.7 | 72.3 | 69.9 |
|  | 3 | 50 | 95.9 | 70.0 | 67.1 |
|  | 4 | 60 | 95.7 | 68.5 | 65.6 |

Each reaction was carried out according to Examples 1-8 and Comparative Examples 1-4. As is clear from Table 1, the steady state of reaction can be maintained in the reactor, the conversion ratio of formaldehyde was always not less than 98% and the yield of isoprene was always not less than 71%, by maintaining the concentration of high boiling point byproducts in the reaction mixture within the range of 0.5-40 mass % (Examples 1-8).

From these results, it was found that isoprene can be efficiently produced while maintaining the steady state of reaction by maintaining the concentration of high boiling point byproducts in the reaction mixture within the range of 0.5-40 mass %.

In contrast, in Comparative Examples 1-4 where the concentration of high boiling point byproducts in the reaction mixture was outside the above-mentioned range, the conversion ratio of formaldehyde was below 97% and the yield of isoprene was always less than 70% in all examples.

In addition, in Comparative Examples 1 and 2 where the concentration of high boiling point byproducts in the reaction mixture was less than 0.5 mass %, the efficiency of heating the reaction mixture in the heat exchanger 3 decreased, resulting in a lower temperature of the reaction mixture in the reactor, which in turn decreased the conversion ratio of formaldehyde, and the yield became lower.

In Comparative Examples 3 and 4 where the concentration of high boiling point byproducts was set to a value exceeding 40 mass %, the high boiling point byproducts were accumulated in the pipe line connecting the reactor 1 and heat exchanger 3, and delivery of the reaction mixture to the heat exchanger 3 became difficult, which in turn resulted in lower efficiency of heating the reaction mixture in the heat exchanger 3. Therefore, the temperature of the reaction mixture in the reactor decreased, which in turn decreased the conversion ratio of formaldehyde and selectivity of isoprene, and the yield became lower.

The process for producing isoprene of the present invention is advantageous in that the production steps are simple, and further, utility can be suppressed low as compared to other known production methods of isoprene (e.g., JP-A-56-79628 and HYDROCARBON PROCESSING, page 167, November, 1971). The successful increase in the yield of about 2% by this method, which could not be accomplished heretofore, is highly useful in the field of the present invention also from the aspect of production cost.

INDUSTRIAL APPLICABILITY

Isoprene obtained by the production method of the present invention can be effectively used as a basic chemical starting material for various chemical products and starting material of polymers.

The invention claimed is:

1. A process for producing isoprene, which comprises continuously or intermittently supplying isobutylene and/or t-butanol, formaldehyde and water into an acidic aqueous solution, and reacting the reaction mixture while distilling away a mixture comprising produced isoprene, water, unreacted starting materials and other low boiling point components from this reaction mixture to the outside of the reaction system, wherein said reaction is carried out while controlling the concentration of high boiling point byproducts, which is produced and accumulated in said reaction mixture, to fall within the range of 0.5-40 mass %.

2. A process for producing isoprene, which comprises continuously or intermittently supplying isobutylene and/or t-butanol, formaldehyde and water into an acidic aqueous solution, and reacting the reaction mixture while distilling away a mixture comprising produced isoprene, water, unreacted starting materials and other low boiling point components from this reaction mixture to the outside of the reaction system, wherein said reaction is carried out while controlling the concentration of high boiling point byproducts, which are produced and accumulated in the reaction mixture, to fall within the range of 0.5-40 mass % by forming an outlet/outlets for taking out the reaction mixture in a reactor containing the reaction mixture, taking out a part of the reaction mixture from the outlet, and separating and removing at least a part of the high boiling point byproducts from the reaction mixture, since then introducing the left reaction mixture again into the reactor.

3. A process for producing isoprene, which comprises continuously or intermittently supplying isobutylene and/or t-butanol, formaldehyde and water into an acidic aqueous solution, and reacting the reaction mixture while distilling away a mixture comprising produced isoprene, water, unreacted starting materials and other low boiling point components from this reaction mixture to the outside of the reaction system, wherein said reaction is carried out while controlling the concentration of high boiling point byproducts, which is produced and accumulated in the reaction mixture, to fall within the range of 0.5-40 mass % by forming an outlet for taking out the reaction mixture at least in the bottom of the reactor containing the reaction mixture, taking out a part of the reaction mixture from the outlet, and separating and removing at least a part of the high boiling point byproducts from the reaction mixture, since then introducing the left reaction mixture again into the reactor.

4. A process for producing isoprene, which comprises continuously or intermittently supplying isobutylene and/or t-butanol, formaldehyde and water into an acidic aqueous solution, and reacting the reaction mixture while distilling away a mixture comprising produced isoprene, water, unreacted starting materials and other low boiling point components from this reaction mixture to the outside of the reaction system, wherein said reaction is carried out while controlling the concentration of high boiling point byproducts, which is produced and accumulated in the reaction mixture, to fall within the range of 0.5-40 mass % by forming an outlet for taking out the reaction mixture in the side wall of the reactor, and the level of the outlet is set such that the volume of the reaction mixture filled to the level is not less than ½ of the total volume of the reaction mixture during the production of isoprene, taking out a part of the reaction mixture from the outlet, and separating and removing at least a part of the high boiling point byproducts from the reaction mixture, since then introducing the left reaction mixture again into the reactor.

5. The process according to claim 1, wherein the mixture containing produced isoprene, water, unreacted starting materials and other low boiling point components is distilled away from the reaction system as a reaction distillation gas, water is fractionally condensed from the reaction distillation gas, and the obtained water is introduced into the reactor again to control the concentration of the high boiling point byproducts in the reaction mixture to fall within said range.

6. The process according to claim 1, wherein said reaction is carried out while controlling the concentration of high boiling point byproducts, which are produced and accumulated in the reaction mixture, to fall within said range by installing, on the reactor, a stirring apparatus having a stirring blade designed to horizontally rotate in the reaction mixture, and supplying isobutylene and/or t-butanol toward the stirring blade from an inlet formed by extending a pipe line to directly below the stirring blade in the reactor.

7. The process according to claim 1, wherein the concentration of the high boiling point byproducts in the reaction mixture is controlled to fall within said range by installing, on the reactor, a stirring apparatus having a stirring blade designed to horizontally rotate in the reaction mixture, in which a part of the reaction mixture is taken out from the reactor, heated with at least a part of isobutylene and/or t-butanol in a heat exchanger and introduced again into the reactor, and supplying the heated reaction mixture toward the stirring blade from an inlet formed in the reactor.

8. The process according to any of claims 2-4, wherein the mixture containing produced isoprene, water, unreacted starting materials and other low boiling point components is distilled away from the reaction system as a reaction distillation gas, water is fractionally condensed from the reaction distillation gas, and the obtained water is introduced into the reactor again to control the concentration of the high boiling point byproducts in the reaction mixture to fall within said range.

9. The process according to any of claims 2-5, wherein the concentration of the high boiling point byproducts in the reaction mixture is controlled to fall within said range by installing, on the reactor, a stirring apparatus having a stirring blade designed to horizontally rotate in the reaction mixture, and supplying isobutylene and/or t-butanol toward the stirring blade from an inlet formed by extending a pipe line to directly below the stirring blade in the reactor.

10. The process according to any of claims 2-6, wherein the concentration of the high boiling point byproducts in the reaction mixture is controlled to fall within said range by installing, on the reactor, a stirring apparatus having a stirring blade designed to horizontally rotate in the reaction mixture, in which a part of the reaction mixture is taken out from the reactor, heated with at least a part of isobutylene and/or t-butanol in a heat exchanger and introduced again into the reactor, and supplying the heated reaction mixture toward the stirring blade from an inlet formed in the reactor.

* * * * *